United States Patent
Woodroof

(10) Patent No.: US 9,017,405 B2
(45) Date of Patent: Apr. 28, 2015

(54) SKIN SUBSTITUTE AND WOUND DRESSING WITH VARIABLE PORE SIZES

(71) Applicant: E. Aubrey Woodroof, Carlsbad, CA (US)

(72) Inventor: E. Aubrey Woodroof, Carlsbad, CA (US)

( * ) Notice: Subject to any disclaimer, the term of this patent is extended or adjusted under 35 U.S.C. 154(b) by 0 days.

(21) Appl. No.: 13/897,430

(22) Filed: May 19, 2013

(65) Prior Publication Data

US 2014/0343676 A1    Nov. 20, 2014

Related U.S. Application Data

(60) Provisional application No. 61/773,707, filed on Mar. 6, 2013.

(51) Int. Cl.
| | |
|---|---|
| A61F 2/10 | (2006.01) |
| A61F 13/00 | (2006.01) |
| A61L 15/26 | (2006.01) |
| A61F 13/02 | (2006.01) |
| A61L 27/60 | (2006.01) |
| A61L 26/00 | (2006.01) |

(52) U.S. Cl.
CPC ............... *A61L 15/26* (2013.01); *A61F 13/02* (2013.01); *A61L 27/60* (2013.01); *A61L 26/0019* (2013.01); *A61L 26/0066* (2013.01); *A61L 26/0085* (2013.01); *A61L 2300/30* (2013.01)

(58) Field of Classification Search
USPC ............ 623/1.41, 15.11–15.12, 23.72–23.76, 623/926; 424/443, 447; 435/396–408; 602/42–47
See application file for complete search history.

(56) References Cited

U.S. PATENT DOCUMENTS 5,584,801 A * 12/1996 Kuroyanagi et al. ............ 602/47
7,815,931 B2 * 10/2010 Woodroof et al. ............. 424/447

* cited by examiner

*Primary Examiner* — Yashita Sharma
(74) *Attorney, Agent, or Firm* — Steven W. Webb

(57) ABSTRACT

An improved skin substitute is presented comprised of a silicone layer backed up with a woven nylon fabric layer, the silicone layer possessing a regular pattern of slits that permit the porosity of the skin substitute to be adjusted by clinicians by means of applying tension to the skin substitute that differentially opens the slits. A variety of therapeutic substances can be applied to the skin substitute to promote healing, including aloe and other medicinal preparations.

3 Claims, 2 Drawing Sheets

SKIN SUBSTITUTE AND WOUND DRESSING WITH VARIABLE PORE SIZES

RELATED APPLICATIONS

This application claims the benefit of Provisional Patent Application 61/773,707, filed Mar. 6, 2013.

FIELD OF THE INVENTION

This invention relates to dressings and bandages for acute and chronic wounds.

BACKGROUND OF THE INVENTION

Wound management involves removal of all non-viable tissue at the wound site, preserving the remaining viable tissue, and providing a moist but not wet environment. An example of successful burn wound dressing is Biobrane, granted U.S. Pat. No. 4,725,279. In 1979 Biobrane was initially studied by American Burn Surgeons; it is still popular world-wide.

In 2007 new art was introduced by this inventor with AWBAT and then with AWBAT Plus, granted U.S. Pat. No. 7,815,931 and covered by several copending patent applications. The key to the success of these products was better porosity in the dressing.

Recently, this inventor has revisited the art of dressing design. The present invention allows passage of fluid adjacent to the wound through the primary dressing into a secondary absorbent dressing as well as improving the kinetics of uninterrupted wound healing. Technology of this dressing has evolved into a new product which possesses all the characteristics and attributes known to be important for optimal wound healing, as well as containing certain advances that result in minimization of wound desiccation and infection complication.

SUMMARY OF THE INVENTION

Wound sites have variable amounts of exudate/transudate/plasma present, from dry to weepy. The clinician must cleanly debride the wound, close it and manage wound healing in a moist but not wet environment to achieve optimal results in both acute and chronic wounds.

The present invention provides a dressing that possesses all the properties and attributes of an ideal skin substitute and, in addition, has 'variable porosity' controlled by the clinician from zero porosity to what the wound requires. The present invention enables the clinician to move the fluid exuding from the wound through the primary dressing into an absorbent secondary dressing without disturbing the kinetics of healing or causing pain to the patient.

The present invention is cost effective at every level. Patients get their wounds managed with minimal pain and optimal healing times. The dressing is cost effective as the hospital needs to inventory only one primary dressing for acute wounds (burns) and one for chronic wounds; each has a two year shelf-life at room temperature.

The present invention is composed of two biological layers sprayed on in separate operations. The first layer sprayed onto the nylon side of the "variable porosity" silicone membrane will be: (1) a solution of pure Aloe (Aloesin, Immuno10, Qmatrix and Loesyn—each hydrophilic and hygroscopic.); (2) a solution of pure Aloe and hypoallergenic USP Pharmaceutical Grade porcine gelatin; or (3) a fine suspension of pure Aloe, gelatin and ECM (as fine insoluble particles or hollow spheres in water—the latter possesses improved healing properties). In vitro, the Aloe component has been demonstrated to cause a variety of cells to attach and proliferate; as well as increase synthesis of collagen and alpha smooth muscle actin. ECM may be added to the biologicals described above and is a mixture from human fibroblasts that is known to cause rapid cell proliferation and tissue growth. Previous wound dressings and skin substitutes, as taught in U.S. Pat. No. 7,815,931 contain gelatin, a pure Aloe component, chondroitin 4 & 6 sulfate, and vitamin C & E. In contrast the current dressing will have two layers of biologicals applied in separate spraying operations as described above. The first coat will contact the wound after the second coat of hypoallergenic bovine spongiform encephalopathy (BSE)-free United States Pharmaceutical (USP)-grade gelatin interacts with fibrin in the wound to achieve early adherence, The second coat of biologicals stimulates the healing process during the interval where the dressing invention is in contact with the wound and is stable requiring 100 degree water for 30 minutes to remove from the "variable porosity" silicone/nylon surface.

DETAILED DESCRIPTION

Figure 1:
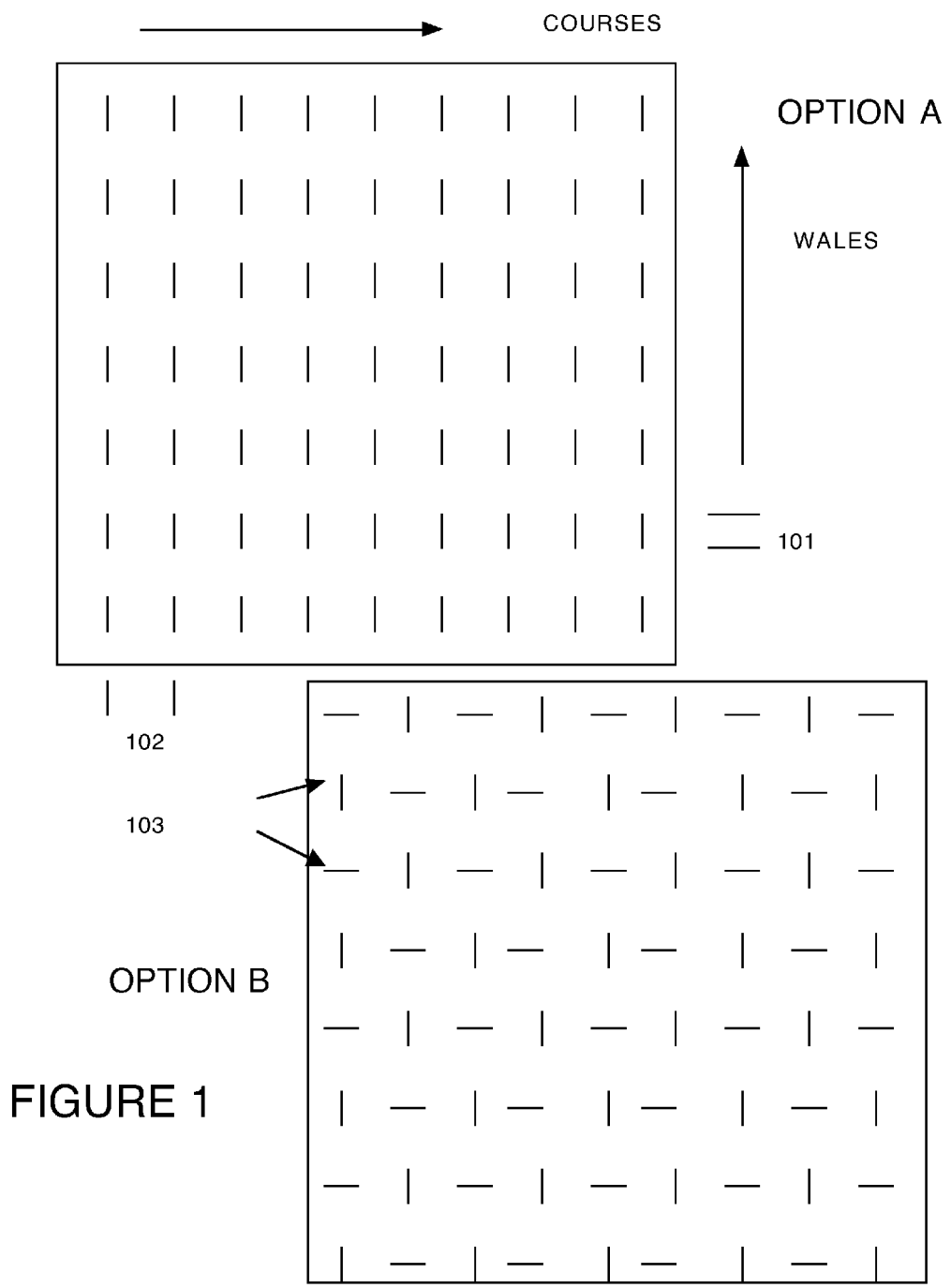
FIG. 1. The embodiments of the invention, showing the slit openings

The present invention is similar in composition to earlier skin substitutes in that they each have a thin silicone component and an underlying thin knitted nylon component. The present invention differs from its ancestors in that it has "variable porosity" controlled by the clinician; the pore size in the thin silicone will be essentially zero (with no stretch, in relaxed mode) to a higher porosity (proportional to the stretch applied). See FIG. 1 for the optional stretch modes. In addition, the present invention differs in the composition of biological coatings applied to both components and how these coatings interact with the wound over time.

The pores of prior art skin substitutes/dressings are of a fixed size (Biobrane 1.2%; AWBAT and AWBAT Plus 5.5% and 7.5%) in the unstretched open position; the silicone is cured while the skin substitute pores are open. Once cured the pores cannot close or be reduced in size; this causes wound desiccation and punctate scarring. As in FIG. 1, in contrast, the openings are made after the silicone component has been cured, and are in the shape of slits, not holes. The figure shows the skin substitute silicone layer up with the slits exposed.

Figure 2:
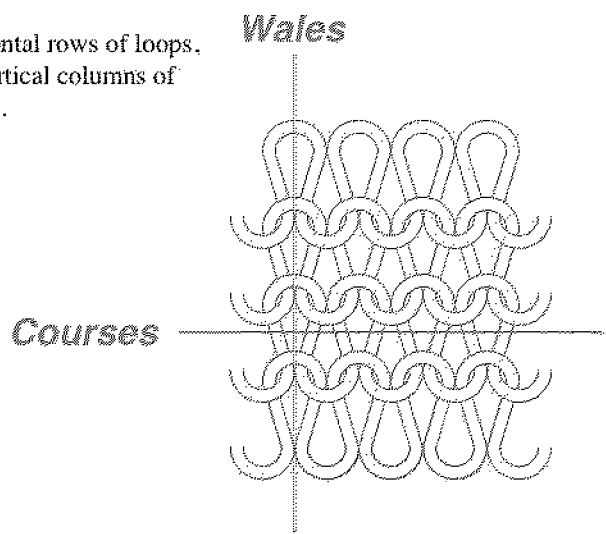
FIG. 2. The wale and course nature of the woven fabric

The "wale" and "course" orientations of stitching of the knitted nylon component of the invention are shown in FIG. 2. The two embodiments of the invention are shown in FIGS. 1A and 1B. In one embodiment, Option A—designed for burns, the slits 103 made in the silicone are approximately 0.125" long 101 with a space of 0.25" between slits 102; parallel rows of slits are 0.25" apart. The parallel rows of slits are oriented such that the slits are parallel to the "wale" orientation of the Jersey stitch pattern of the knitted nylon component. The "wale" orientation has measurably less elongation than the "course" orientation.

Because of the orientation of the slits, stretch along the axis of the slits is minimal and stretch perpendicular to the slit axes is maximized. With no stretch of the silicone/nylon membrane the slits cannot be seen without magnification while observing from above.

In the second embodiment, Option B—designed for chronic wounds, a less regular pattern with slits both parallel and perpendicular is preferred. The slits made in the silicone are approximately 0.125" long with a space of 0.50", between the slits; off-set parallel rows of slits are 0.25" apart. Rows of slits perpendicular to the above are also 0.125" long with a space of 0.50", between the next slit; off-set parallel rows of slits are 0.25" apart. In this configuration the silicone/nylon membrane can be stretched in any direction and the slits will open. Porosity therefore increases proportional to the amount of stretch applied. Obviously, there is a maximum amount of stretching of the Option B invention before the dressing fails.

For burns, Option A is preferable, particularly on partial thickness burns where punctate scarring has been observed. In the Option A configuration, with no stretch, the wound is protected by an essentially continuous thin silicone membrane which minimizes wound desiccation and punctate scarring. Option A enables the clinician to stretch the dressing parallel to the direction of the slits with minimal opening of the slits. This is parallel to the "wale" direction of the underlying fabric. Fluids from the wound can still escape through the closed slits and be absorbed into a secondary dressing, which can be removed and replaced without interfering with the healing process or causing pain to the patient.

Figure 3:
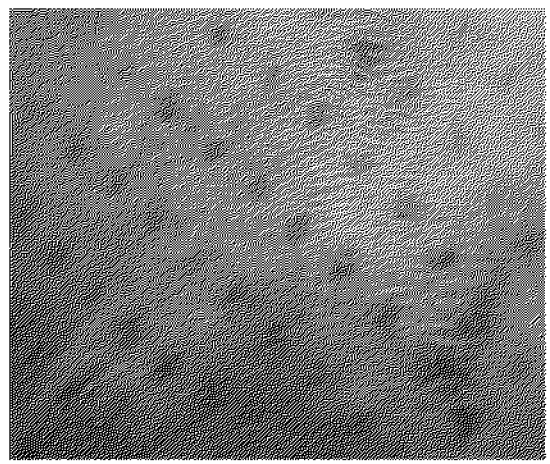
FIG. 3. An example of punctuate scarring

The combination of a primary dressing that requires minimal changes and a secondary dressing that is easy to change and replace reduces wound maintenance costs which benefits patient, staff and hospital. An example of punctate scarring is illustrated in FIG. 3; the figure shows the skin of a patient whose burn was covered with the ancestor AWBAT dressing with a fixed porosity of at least 5.5%.

Chronic, slow healing wounds require similar treatment as burns in that all necrotic tissue must be removed before closing the wound with a primary dressing. In the chronic wound, exudate and other fluids are often removed with negative pressure wound therapy (NPWT). A negative pressure above the wound or a positive pressure from the wound causes exudate and other wound fluids to pass through the primary dressing into a secondary dressing. The primary dressings currently used during NPWT are: urethane foam, polyvinyl alcohol foam or cotton gauze; all require frequent dressing changes and infection complications have been reported when these dressings are not changed frequently.

The use of the present invention has a large benefit because it is stable on the wound, compatible with or without NPWT, and possesses biologicals that aid in the healing process. Option B of the invention is preferred for closing the chronic wound because it provides greater porosity as well as an increased rate of porosity, compared to Option A, when the dressing is stretched in any direction the appropriate amount. Since chronic wounds are generally in the lower extremities, punctate scarring is not a clinical concern. An example of chronic wounds that benefit from this novel art are: pressure sores, diabetic ulcers and chronic vascular ulcers.

The present invention will have two layers of biologicals; first a clotting outer layer containing hypoallergenic BSE free USP Pharmaceutical grade gelatin. This layer contacts the wound first and stimulates initial adherence of the dressing to the cleanly debrided wound. The second layer of pure Aloe or Aloesin, pure Aloe and BSE free gelatin, or a mixture of pure Aloe, BSE free gelatin and ECM interact with the wound to stimulate the rate of healing while adherent to the wound. The first layer is deposited directly on the nylon side of the "variable porosity" silicone/nylon surface and is stable, i.e. requires 100 degree water for 30 minutes to remove from the "variable porosity" silicone/nylon surface.

These are the preferred embodiments of the invention. The technology to create the two forms of the invention is listed as the preferred embodiments of this invention, but other methods are possible and are within the contemplation of this patent.

What is claimed is:

1. A skin substitute, the skin substitute comprised of two layers of material,
the first layer of material, an upper layer, comprised of a silicone membrane, the second layer, a lower layer, comprised of a woven nylon fabric,
the silicone membrane selected in a thickness from 0.001" to 0.005",
the upper layer possessing a plurality of slits in its surface, said slits made after the two layers are joined together, said slits in a pattern comprised of multiple rows of parallel slits,
the lower layer woven in a regular pattern with a perpendicular wale and course orientation, the slits on the surface either following the wale direction of the lower layer or crossing the wale direction of the lower layer perpendicularly,
said upper layer and said lower layer treated with a plurality of layers of medicinal or therapeutic substances applied to the two layers of the skin substitute,
said slits placed in said upper layer such that the skin substitute has essentially zero porosity with no stretching tension placed on it, the porosity of said skin substitute variable proportional to the amount of stretching tension and the direction in which said stretching tension is placed on the skin substitute,
the direction of stretching tension dependent on the orientation of said slits with the wale and course orientation of the woven nylon fabric,
the skin substitute designed to place the woven nylon fabric side down on top of a wound when in use,
the skin substitute selected to be used in combination with an absorptive dressing placed above said skin substitute over the wound.

2. The skin substitute of claim 1 where the plurality of slits are oriented in parallel with the wale orientation of the lower layer.

3. The skin substitute of claim 1 where the plurality of layers of medicinal and therapeutic substances are selected from the list of hypoallergenic BSE free USP Pharmaceutical grade gelatin, pure aloe, aloesin and ECM.

* * * * *